United States Patent
Hani et al.

(10) Patent No.: US 9,820,481 B2
(45) Date of Patent: Nov. 21, 2017

(54) ENCAPSULATION OF ACTIVE INGREDIENTS AND METHOD OF MAKING

(71) Applicant: Arch Chemicals, Inc., Atlanta, GA (US)

(72) Inventors: Rahim Hani, Alpharetta, GA (US); Lianjun Shi, Cumming, GA (US)

(73) Assignee: ARCH CHEMICALS, INC., Atlanta, GA (US)

( * ) Notice: Subject to any disclaimer, the term of this patent is extended or adjusted under 35 U.S.C. 154(b) by 106 days.

(21) Appl. No.: 14/776,804

(22) PCT Filed: Mar. 14, 2014

(86) PCT No.: PCT/US2014/027763
§ 371 (c)(1),
(2) Date: Sep. 15, 2015

(87) PCT Pub. No.: WO2014/143695
PCT Pub. Date: Sep. 18, 2014

(65) Prior Publication Data
US 2016/0037767 A1 Feb. 11, 2016

Related U.S. Application Data

(60) Provisional application No. 61/788,388, filed on Mar. 15, 2013.

(51) Int. Cl.
*A01N 25/28* (2006.01)
*A01N 55/02* (2006.01)
*A01N 43/68* (2006.01)
*A01N 47/30* (2006.01)
*C08J 9/00* (2006.01)
*C08K 9/10* (2006.01)

(52) U.S. Cl.
CPC ............ *A01N 25/28* (2013.01); *A01N 43/68* (2013.01); *A01N 47/30* (2013.01); *A01N 55/02* (2013.01); *C08J 9/009* (2013.01); *C08K 9/10* (2013.01); *C08J 2375/08* (2013.01)

(58) Field of Classification Search
CPC ........ A01N 25/28; A01N 43/68; A01N 47/30; A01N 55/02; C08J 9/009; C08J 2375/08; C08K 9/10
See application file for complete search history.

(56) References Cited

U.S. PATENT DOCUMENTS

| | | | |
|---|---|---|---|
| 4,464,317 A | 8/1984 | Thies et al. | |
| 5,009,700 A * | 4/1991 | Rothgery | A01N 43/40 504/126 |
| 5,284,649 A * | 2/1994 | Juneja | A61K 8/0229 424/67 |
| 6,294,589 B1 | 9/2001 | Moody | |
| 7,429,392 B2 * | 9/2008 | Baum | A01N 25/28 424/405 |
| 8,110,284 B2 | 2/2012 | Naigertsik et al. | |
| 8,685,908 B2 | 4/2014 | Smith, III et al. | |
| 8,901,203 B2 | 12/2014 | Gruzins et al. | |
| 9,131,681 B2 | 9/2015 | Finnie et al. | |
| 2003/0118664 A1 | 6/2003 | Trogolo et al. | |
| 2007/0053950 A1 | 3/2007 | Gajanan et al. | |
| 2008/0254082 A1 | 10/2008 | Toledano et al. | |
| 2011/0177951 A1 | 7/2011 | Toledano et al. | |
| 2012/0219610 A1 | 8/2012 | Smith, III et al. | |
| 2013/0303503 A1 | 11/2013 | Smith, III et al. | |

FOREIGN PATENT DOCUMENTS

WO WO2005/123818 12/2005

OTHER PUBLICATIONS

PCT/US2014/027763, International Search Report and Written Opinion dated Jun. 20, 2014, 17 pages.
Kim S G et al: Characterization of silica-coated Ag nanoparticles synthesized using a water-soluble nanaoparticle micelle Advanced Powder Technology, VSP, Utrecht, NL, vol. 20, No. 1, Jan. 1, 2009, p. 94-100.
Christian Graf, et al.: "A General Method to Coat Colloidal Particles with Silica", Langmuir, vol. 19, No. 17, Aug. 1, 2003, pp. 6693-6700.
Eva Wallstrom et al., A New concept for anti-fouling paint for yachts, Science Digest, Progress in Organic Coatings 72 (2011) pp. 109-114, Mar. 2011.
Written Opinion for Singapore Application No. 11201507540W, dated Dec. 19, 2016, 5 pages.

* cited by examiner

*Primary Examiner* — Irina S Zemel
(74) *Attorney, Agent, or Firm* — Dority & Manning, P.A.

(57) ABSTRACT

A method of preparing a silicon-containing polymeric structure coated/encapsulated active ingredient is disclosed. The method has the steps of providing an insoluble active ingredient; dispersing the active ingredient in a liquid medium to form a suspension of the active ingredient; adding a silicon-containing polymeric structure precursor to the suspension; and reacting the precursor to form the silicon-containing polymeric structure. The silicon-containing polymeric structure is formed around the active ingredient, thereby forming a silicon-containing polymeric structure coated/encapsulated active ingredient. The silicon-containing polymeric structure coated/encapsulated active ingredient may be used in place of the active ingredient itself.

19 Claims, 6 Drawing Sheets

ENCAPSULATION OF ACTIVE INGREDIENTS AND METHOD OF MAKING

RELATED APPLICATIONS

This present application claims priority to and the filing benefit to U.S. Provisional Application No. 61/788,388 filed Mar. 15, 2013 and PCT International Patent Application No. PCT/US2014/027763 filed on Mar. 14, 2014, and which are both hereby incorporated by reference in their entirety.

FIELD OF INVENTION

The present invention relates to an encapsulated active ingredient, the method of making the encapsulated active ingredient and the methods of using the encapsulated active ingredient.

BACKGROUND OF THE INVENTION

Antimicrobial active ingredients have been used in a wide variety of applications. Recently, there has been an increased interest in encapsulating active ingredients for various reasons, including managing active ingredient release from compositions. On particular active ingredient of interest are metal pyrithiones.

Metal pyrithione compounds, such as zinc pyrithione, have been used as an active ingredient in a wide variety of uses, including as anti-dandruff agents, and as anti-fungal, anti-mildew and/or anti-microbial additives to plastics, paints and coatings. However, adding zinc pyrithione to plastics, in particular chlorine containing plastics, such as polyvinylchloride (PVC), results in the problem of yellowing of the plastic. This is especially true for those formulations which are calendared or extruded at high temperatures and/or high shear. This yellowing problem also exists in plastics containing chlorides when the plastic is exposed to light.

Not wishing to be bound by theory, it is believed that high temperature, high shear and/or light may cause hydrochloric acid (HCl) to be formed in the polymer matrix. When HCl is formed, the zinc in the zinc pyrithione may react with hydrochloric acid formed in the PVC, thereby forming zinc chloride. Zinc chloride in the polymer matrix, in turn, tends to catalyze the degradation of the polyvinylchloride, thereby causing the yellowing.

In order to stabilize chlorine containing polymers against degradation when a pyrithione containing compound is added to provide mildew resistance, fungal resistance and antimicrobial properties, it has become necessary to add a scavenger for HCl into the polymer matrix. As such, adding additional ingredients may make it more difficult to process the chloride containing polymer, as well as to add cost to the final product.

Accordingly, there is a need in the art for a pyrithione additive for chlorine containing polymers which does not require the addition of further ingredients to stabilize the chloride containing polymer from degradation.

In addition, there is a need in the art for stabilized or encapsulated active ingredients in other uses, including but not limited to, providing antimicrobial properties to other polymers, such as polyurethanes, in architectural coating, in antifouling paints, in personal care products, such as shampoos and the like.

SUMMARY OF THE INVENTION

In one aspect, the present invention provides a method of preparing an active ingredient which is encapsulated or coated with a silicon-containing polymeric structure. The method has the steps of providing an active ingredient; dispersing the active ingredient in liquid medium in which the active ingredient is insoluble to form a suspension of the active ingredient; adding a silicon-containing polymeric structure precursor to the suspension; and reacting the precursor in the presence of the active ingredient to form a silicon-containing polymeric structure. The silicon-containing polymeric structure is formed around the active ingredient, thereby forming a silicon-containing polymeric structure encapsulated or coating the active ingredient.

In addition, the present invention also provides an active ingredient which is encapsulated with silicon-containing polymeric structure. The active ingredient has an outer surface; a surfactant applied to the outer surface; and silica applied to the surfactant such that the silicon-containing polymeric structure at least partially surrounds the active ingredient.

Also provided by the present invention is a polymer matrix having the active ingredient which is encapsulated with silicon-containing polymeric structure blended with the polymer matrix. The polymer matrix may be used for coatings, molded articles and the like.

These and other aspects will become apparent when reading the detailed description of the invention.

DETAILED DESCRIPTION OF THE INVENTION

Figure 1:
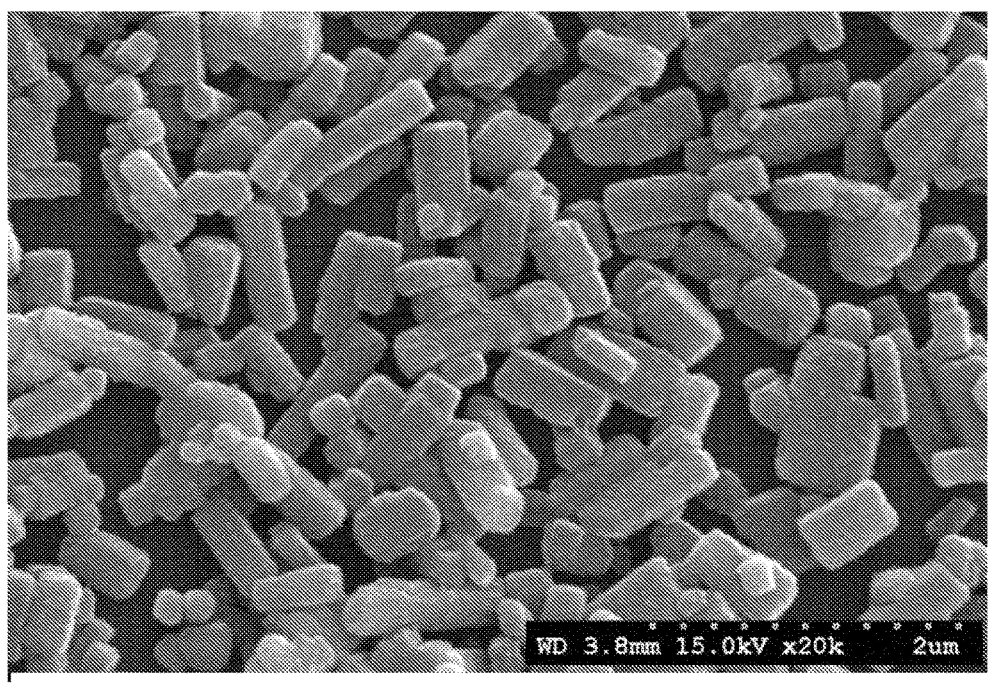
FIG. 1 shows a micrograph of zinc pyrithione particles encapsulated with a silicon-containing polymeric structure using a scanning electron microscope.

It has now been surprisingly found that biocidal active ingredients encapsulated with a silicon-containing polymeric structure provide an active ingredient in a stabilized form which are stable in chloride containing polymers. In addition, it has been discovered that biocidal active ingredients encapsulated with a silicon-containing polymeric structure can be used to replace the "naked" biocide (biocide without an encapsulation in various applications including polyurethanes.

In the present invention, generally the active ingredient is a water insoluble active ingredient. As used herein, the term "biocidal active ingredient" is intended to mean an ingredient which has biocidal properties, including, but not limited to active ingredients that are antimicrobial, sporicidal, fungicidal and the like. For example, suitable water-insoluble active ingredients include pyrithione compounds, basic copper carbonate, isothiazolinone compounds, substituted triazines, carbamates, chlorinated aromatic ureas, triazoles and combinations thereof. Examples of pyrithione compound include metal pyrithione compounds such as zinc pyrithione, copper pyrithione, zirconium pyrithione and the like. Examples of isothiazolinone compounds include, for example, 4, 5-Dichloro-2-n-octyl-4-isothiazolin-3-one (DCOIT), 1,2-benzisothiazolin-3-one (BIT), n-butyl isothiazolinone (BBIT), n-octyl isothiazolinone (OIT) and mixtures thereof. Substituted triazines include, for example, terbutryn (2-tert-butylamino-4-ethylamino-6-methylthio-1, 3,5-triazine). Carbamates include, for example iodopropynyl butylcarbamates (IPBC). Chlorinated aromatic ureas, include, for example, diuron (dichlorophenyl dimethylurea). Of the pyrithione compounds, generally, zinc pyrithione is used from the standpoint of cost and effectiveness. Depending on the intended use of the encapsulated active ingredient, those skilled in the art would be able to determine which active ingredients could be used in the present invention.

The silicon-containing polymeric structure encapsulated active ingredient has silicon-containing polymeric structure applied to the surface of the active ingredient such that the silicon-containing polymeric structure at least partially covers the surface of the active ingredient. The silicon-containing polymeric structure may completely coat or otherwise encapsulate the active ingredient compound such that the active ingredient is completely covered with the silicon-containing polymeric structure. Alternatively, the active ingredient may be partially coated or encased with the silicon-containing polymeric structure. It has been discovered, that the silicon-containing polymeric structure encapsulated active ingredients are more stable than the active ingredient compound alone. In particular, the silicon-containing polymeric structure encapsulated active ingredients have been found to have improved heat stability over non-modified active ingredient compounds.

The silicon-containing polymeric structure encapsulating the active ingredient is prepared by polymerizing the polymeric precursor containing silicon in the presence of the active ingredient. One particular silicon-containing polymeric structure used to encapsulate or otherwise coat the active ingredient is a silica structure. Formation of the silica structure is completed by polymerizing silica precursors in the presence of the active. The polymerization of the precursor takes place in a condensation reaction at either an acidic pH or a basic pH. Suitable silica precursors included, silane compounds of the formula (I):

$$Si(Y)_m(X)_n \qquad (I)$$

where Y is a hydrolysable substituent and X is a substituent which is not reactive with the hydrolysable substituent during the polymerization reaction. In addition, m is an integer from 2-4 and n is an integer of 0-2, wherein m+n=4. In addition, the average value of m is at least three. For example, for every mole of silanes with m=2, there will be at least one mole of silanes where m=4. As such, the silanes may be a mixture of silanes, provided that the average value of m is at least 3.

Examples of substituents which are not reactive with the hydrolysable substituents include hydrocarbons, such as alkyl groups, such as methyl, ethyl, propyl, butyl, and the like, alkenyl group, such as vinyl group, and the like, substituted hydrocarbons which are substituted with halogens, amines, carboxylates, sulfonates, glycidoxy, mecapto or other similar groups. Exemplary groups include N-(2-aminoethyl)-3-amino propyl group, 3-acryloxypropyl group, 3-Glycidoxypropyl, 3-Mercaptopropy, 3-Methacryloxypropyl and other similar groups. Generally X may be any group that does not form a Si—OH group when the silane is hydrolyzed. The X groups may be selected so that the biocidal active ingredients encapsulated with the silica are made to be compatible in the final use composition.

Examples of hydrolysable substituents includes, for example, include, but are not limited to, —Cl, —Br, —OR, —OCH$_2$CH$_2$OR, CH$_3$C(=O)O—, RC=N—O—, CH$_3$C(=O)N(CH$_3$)—, and —ONH$_2$, wherein R is C$_1$ to C$_8$ hydrocarbyl group. Generally, the hydrolysable group is an —OR group, where R is a C$_{1-4}$ alkyl group, more particularly is a methyl or an ethyl group. It is also noted that the silanes may be a mixture of silanes having the formula (I). In particular, exemplary silanes are tetraalkoxy silanes, such as tetramethoxysilane, tetraethoxysilane, tetrabutoxysilane and the line. Other suitable silanes include organotrialkoxysilaness, such as, methyltrimethoxysilane and methyltriethoxysilane; and diorganodialkoxysilanes such as dimethyldiethoxysilane, dimethyldimethoxysilane. Other similar silanes which are known to be precursors for silica, including silicates, such as sodium silicate, and partial reaction products of the silanes having formula (I) may be used to form the silica applied to the surface of the active ingredient.

The coated/encapsulated active ingredient also has a surfactant or dispersant applied to the surface of the insoluble active ingredient which makes the insoluble active ingredient dispersible in water or another suitable medium in which the active ingredient is not soluble or has poor solubility. Suitable mediums which may be used to disperse the active ingredient include, alcohols (such as methanol, ethanol, isopropyl alcohol, etc.), water, buffer solutions, (an aqueous solution consisting of a mixture of a weak acid and its conjugate base or a weak base and its conjugate acid), hydrocarbon solvents such as octane, hexane and the like, or mixtures two or more of these solvents.

The surfactant/dispersant can be surfactants which have a hydrophobic segment bearing a positively charged group or bearing groups exhibiting a positive charge in a pH range of about 2 to about 13. Examples of such surfactants include, but are not limited to cetyltrimethylammonium bromide (CTAB), cetyltrimethylammonium chloride (CTAC), Cetyltrimethylammonium hydroxide (CTAOH), Monosodium salt of sulfated methyl oleate (Darvan) and the like. Suitable dispersants include natural polymers and their derivative, as well as synthetic polymers. Each of the natural polymers or synthetic polymers may be a cationic polymer, a neutral polymer or an anionic polymer. Examples of natural polymers and their derivative which may be used in the present invention includes, for example, hydroxymethylcellulose, hydroxyethylcellulose, hydroxypropylcellulose, chitosan, gelatin, gum arabic, just to name a few. Cationic synthetic polymers, include PEI (poly(ethylene imine)), poly(vinylamine), poly(L-lysine), poly(L-arginine), poly (vinyl pyridine), poly(2-dimethylaminoethyl methacrylate)-poly (2-diisopropylamino ethyl methacrylate) (PDMA), poly(diallyldimethylammonium chloride) (PDDA) and other similar cationic polymers polymers. Suitable neutral synthetic polymers include, for example, and polyether containing diblock and triblock copolymers, for example, PEG-b-PPO, and PEO-b-PPO-b-PEO, where PEG is polyethylene glycol, PPO is polypropylene oxide, and PEO is polyethylene oxide; polyvinylpyrrolidone, polyvinyl alcohol, and copolymers thereof; polysiloxanes, such as polydimethylsiloxane. Anionic dispersants include, for example, poly(acrylic acid), polystyrene-polyacrylic acid, polystyrene sulfonic acid sodium salt, and other similar acid containing surfactants/dispersants Another class of surfactants/dispersants includes lipids which have hydrophobic tails with one or more groups exhibiting a positive charge, neutral or a negative charge in the pH range of 2-13. Examples of such lipids include, but not limited to phospholipids such as phoshatidyl ethanolamine, phosphatidyl serine ceramide, phosphonyl glycerol; N-lauroylsarcosine, tetradecyltrimethy ammonium bromide (TTAB), didodecyldimethlammonium bromide (DDAB) and the like. Other Surfactants may be Gemini type surfactants, which have two conventional surfactant molecules chemically bonded together by a spacer.

It has been discovered that lower molecular weight dispersants result in a shell of the silicon-containing polymeric structure having a smooth surface and the higher molecular weights dispersants result in a shell of silicon-containing polymeric structure which is relatively rougher.

The surfactant/dispersants serves to disperse the active ingredient in a liquid medium in which the active ingredient is insoluble and provide a site for the forming silica to anchor itself to the active ingredient. The resulting silicon-containing polymeric structure coated/encapsulated active ingredient has the active ingredient with an outer surface having the surfactant applied to the outer surface. Once the outer surface is treated with the surfactant/dispersant, the silicon-containing polymeric structure is formed and applied to the outer surface by polymerizing the silicon-containing polymeric structure precursor in the presence of the dispersed active ingredient, thereby forming the silica silicon-containing polymeric structure encapsulated active ingredient.

To prepare the silicon-containing polymeric structure coated/encapsulated active ingredient, the following method may be used. The active ingredient is first provided and dispersed in a liquid medium in which the active ingredient is insoluble. Any method can be used to disperse insoluble active ingredient to form a suspension of the active ingredient. Generally, the insoluble active ingredient is mixed with the surfactant mentioned and the liquid medium, and the insoluble active ingredient, surfactant and liquid medium are mixed using the suitable mixing method including, but are not limited to, high-shear mixing and/or sonication. Exemplary high-shear mixing may be accomplished using a stir bar or an overhead mixer. The mixing occurs for a period of time sufficient to form a dispersion or suspension of the insoluble active ingredient in the liquid medium. The period of time may vary depending on the mixing conditions used. For example, the mixing accomplished by sonification may take less time than mixing accomplished using high shear mixing. The result of the mixing is a suspension of the water insoluble active ingredient in the liquid medium.

Once the suspension or dispersion of the active ingredient is formed, next the silicon-containing polymeric structure precursor is added to the suspension. The silicon-containing polymeric structure precursor is then reacted in the presence of the dispersed or suspended active ingredient. Generally, the silicon-containing polymeric structure precursor will be a silica precursor and the process will be described in terms of a silica precursor. To cause reaction of the silica precursor, the pH of the suspension/dispersion is changed to an acidic pH or a basic pH or may be a neutral pH. The pH may be anywhere in the range of about 1 to about 14, Typically, the pH may be within the range of about 3 to about 12. The pH may be modified to an acidic pH, generally a pH in the range of about 3 to about 6, by the addition of an acid, such as acetic acid. Similarly, the pH may be modified to a basic pH, generally in the range of about 8-12, by the addition of a basic component, such as sodium hydroxide, lysine, triethanolamine and the like. The pH may be modified by the addition of a separate ingredient or the pH may be adjusted during the addition of the dispersant to the composition. That is, the dispersant may be an acidic or basic, which causes a pH change. The actual pH used may be dependent on the active ingredient to be encapsulated. The pH may be modified before or after the silica precursor is added to the suspension or dispersion. Generally, the pH is adjusted before the silica precursor is added to the suspension or dispersion. The silica precursor is allowed to react for a period of time. Generally, the reaction will proceed at or about room temperature. Elevated temperature (above room temperature) may also be used. Typically, the temperature will be between room temperature and 90° C. The usual temperature range is between room temperature and about 60° C.

During the reaction of the silica precursor, the mixture of the silica precursor, dispersant/surfactant, active ingredient and water, may be stirred. The reaction of the silica precursor takes place at or near the interface of the active ingredient and the water. As such, as the silica precursor reacts, the silica precursor serves to coat and/or encase the active ingredient within a silica shell. Generally, the resulting product of the reaction of the silica precursor in the presence of the dispersed or suspended active ingredient is an active ingredient that is coated or encapsulated within the silica. In this regard, attention is directed to FIG. 1 which shows silica encapsulated active ingredient, within the scope of the present invention, in this case zinc pyrithione, which is encased or encapsulated with the silica. In addition, FIGS. 2 and 3 show silica encapsulated zinc pyrithione. For comparison purposes FIG. 4 shows zinc pyrithione without being coated or encapsulated with silica. As can be clearly seen, the silica encapsulates or otherwise coats the active ingredient.

Once the reaction has stopped, the silicon-containing polymeric structure or silica encapsulated active ingredient is removed from the liquid medium. Suitable conventional separation techniques, such a filtration, centrifuge, drying and the like or combinations thereof, may be used to remove the liquid medium from the silica encapsulated active ingredient. Generally, the silica encapsulated active ingredient is in the form of a particulate, such as a powder, when the liquid medium is removed.

The silicon-containing polymeric structure encapsulated active ingredient has pores in the silicon-containing outer shell. The pores range from about 0.5 nm to about 100 nm in size. Generally, the pores have a size about 1 to about 25 nm and more typically, about 1-10 microns. The pores in the silicon-containing outer shell allow the silicon-containing polymeric structure encapsulated active ingredient to remain active used as biocidal agent.

The silicon-containing polymeric structure encapsulated active ingredient will general contain up to about 70% by weight of the silicon-containing polymeric structure. In most applications, the silicon-containing polymeric structure content of the silicon-containing polymeric structure encapsulated active ingredient will be between about 1% by weight and about 50% by weight. More typically, the silicon-containing polymeric structure content will be between about 5 and 45% by weight of the silicon-containing polymeric structure encapsulated active ingredient. In a particular embodiment, the silicon-containing polymeric structure will be between about 25 and 45% by weight. As is stated above, the silicon-containing polymeric structure will be generally a silica structure.

The silicon-containing polymeric structure encapsulated active ingredient may be used in place of active ingredient alone. Generally, the silicon containing polymeric structure modified active ingredient may be used in applications where the active ingredient allow cannot be used due to stability issues of the active ingredient. The silicon-containing polymeric structure encapsulated active agent may be blend with a composition which is intended to have biocidial properties. The silica silicon-containing polymeric structure encapsulated active ingredient may be added to a polymer matrix which can be used for a molded article, a coating, a sealant or other similar utilities. In one particular embodiment, the silicon containing polymeric structure encapsulated active ingredient may be added to a polymer matrix which is used to make an article of manufacture. One particular polymer matrix in which the silicon-containing polymeric structure encapsulated active ingredient may be especially useful is chlorine containing polymer matrix, such as polyvinylchloride. This is especially true when the active ingredient is or contains zinc pyrithione.

The present invention is further described in detail by means of the following Examples. All parts and percentages are by weight and all temperatures are degrees Celsius unless explicitly stated otherwise.

EXAMPLES

Example 1. Preparation of Silica-Coated/Encapsulated Zinc Pyrithione

About 3.00 g of zinc pyrithione particles and 40 mL dispersant containing 2% polyvinylpyrrilidone—PVP360 (a polyvinylpyrrilidone having a molecular weight of about 360,000) in an aqueous solution were placed in a 125 mL glass beaker. The mixture was stirred by overhead mixer for two hours at 500 rpm to get homogeneous zinc pyrithione dispersion. The dispersion was next titrated to pH 4.5 with 10% acetic acid under magnetic stirring. After reaching the pH of 4.5, 1.57 g of tetraethoxysilane (TEOS) was added to the beaker. The resulting mixture was stirred on a stir plate at 750 rpm for 16 h, at room temperature or at 60 C, to obtain particles with silica shell and a zinc pyrithione core.

The above example was repeated three additional times to show that the results are repeatable. The results shown in Table 1 establish that the results are repeatable. The degradation temperature was determined by thermal gravimetric analysis (TGA) or differential scanning calorimetry (DSC).

Figure 2:
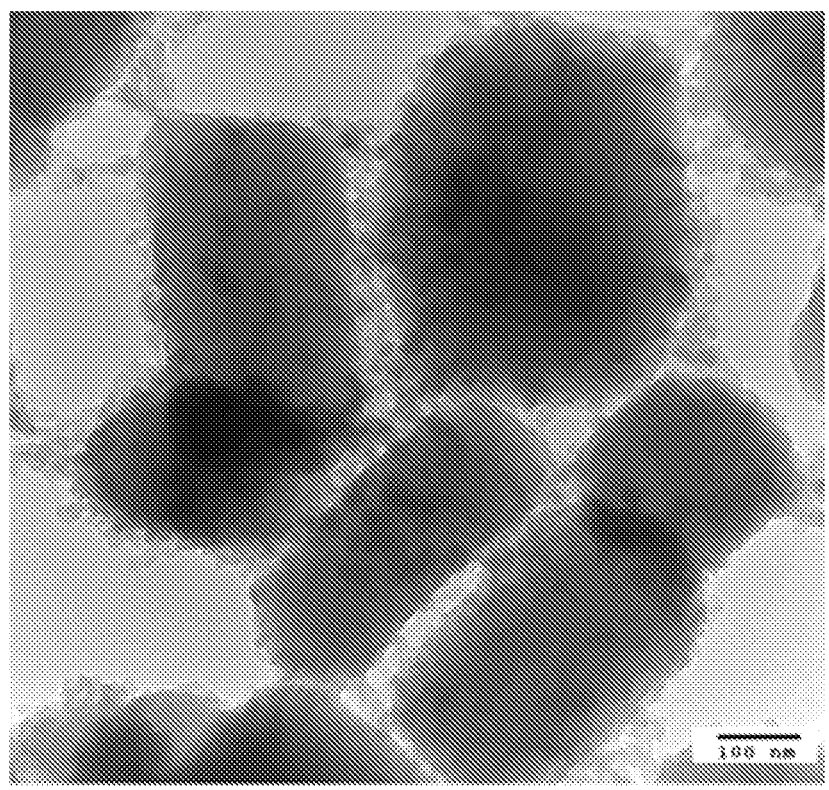
FIG. 2 shows a micrograph of zinc pyrithione particles encapsulated with a silicon-containing polymeric structure using a transmission electron microscope.
Figure 3:
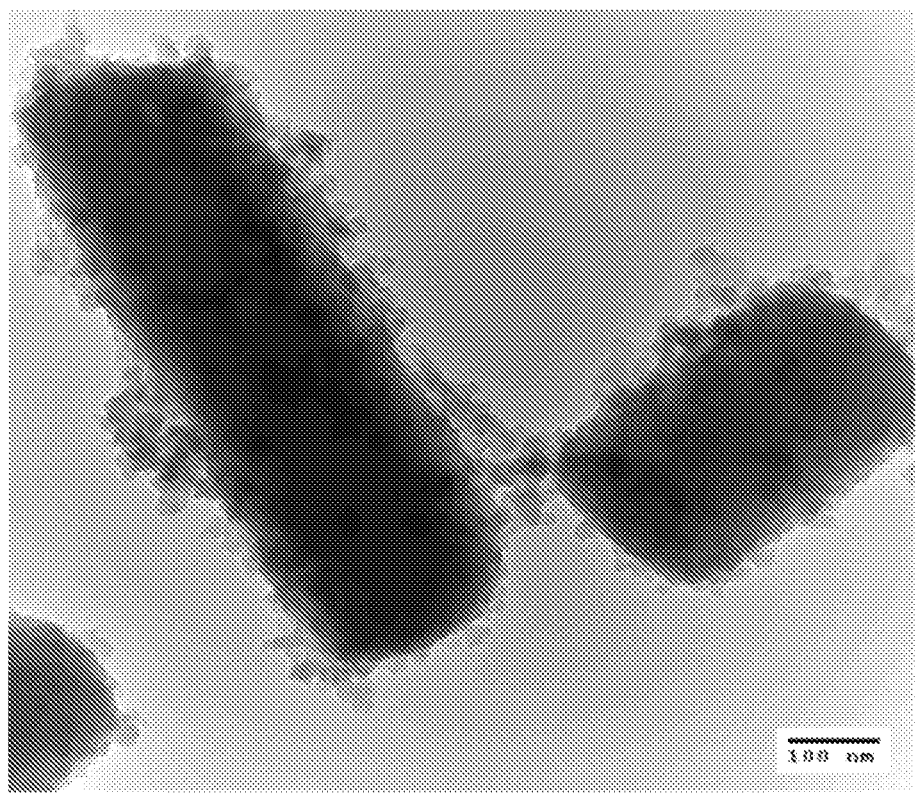
FIG. 3 shows a micrograph of zinc pyrithione particles encapsulated with a silicon-containing polymeric structure using a transmission electron microscope.
Figure 4:
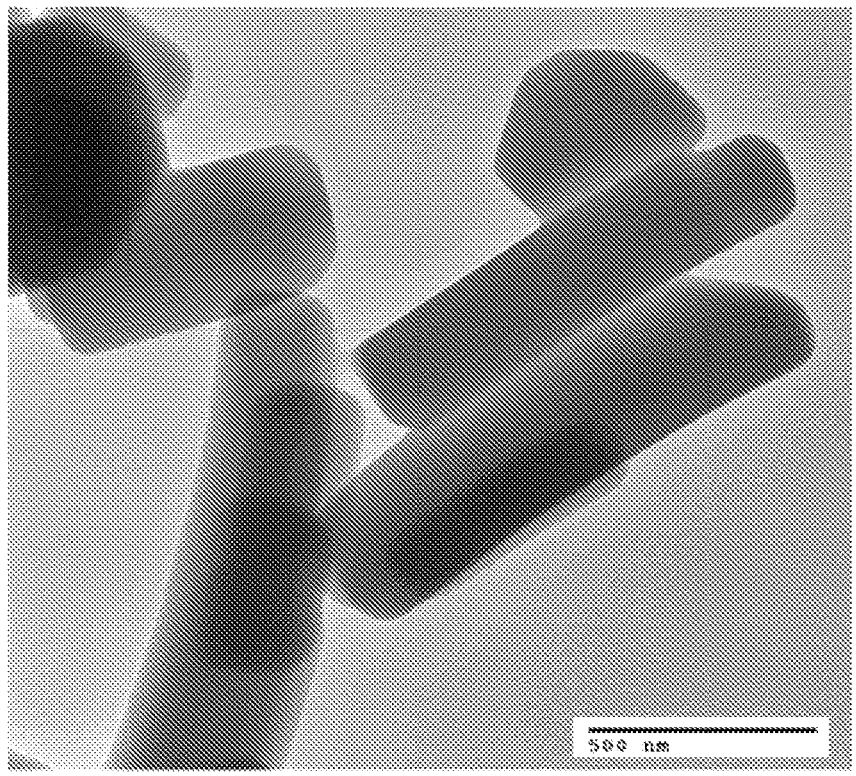
FIG. 4 shows a micrograph of zinc pyrithione particles without a silicon-containing polymeric structure encapsulation using a transmission electron microscope.

FIGS. 1-3 show Sample B under different magnification. The uncoated zinc pyrithione is shown in FIG. 4.

Example 2. Preparation of Silica-Coated/Encapsulated Zinc Pyrithione

Figure 5:
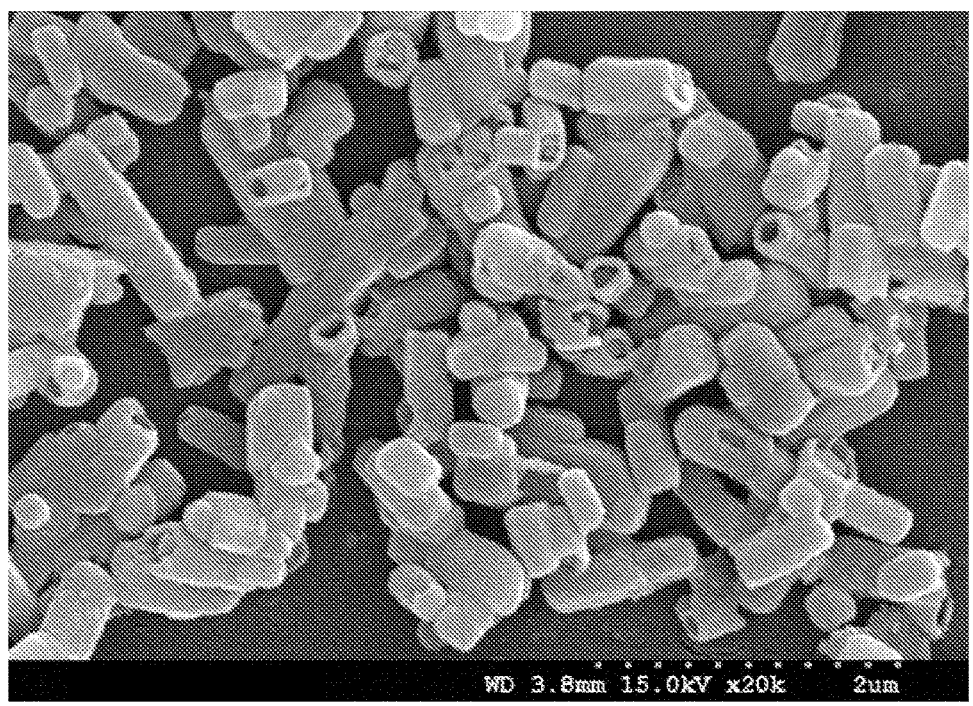
FIG. 5 shows a micrograph of zinc pyrithione particles encapsulated with a silicon-containing polymeric structure made in accordance with Example 2.

About 30 g of Zinc pyrithione particles and 400 mL of 1.1% (PVP Kollidon 17 PF (Polyvinylpyrrolidone; Mw: 10,000) in an aqueous solution were placed in a 1 L round-bottom flask. The mixture was stirred by Silverson high shear mixer at 8000 rpm for 20 min. Then the obtained dispersion was titrated to pH 4.53 with 10% acetic acid under magnetic stirring. After that, 15.7 g of TEOS was added. The mixture was agitated by overhead mixer at 600 rpm for 16 h and said microcapsules were obtained with silica shell and a ZPT core. The capsules had a particle size distribution of d (90%): 8.69 μm; d (50%): 5.93 μm; d (10%): 3.73 μm. The capsules contained ZnPT=80%, silica=20%. An SEM of the coated/encapsulated zinc pyrithione is shown in FIG. 5 for comparison purposes.

Figure 6:
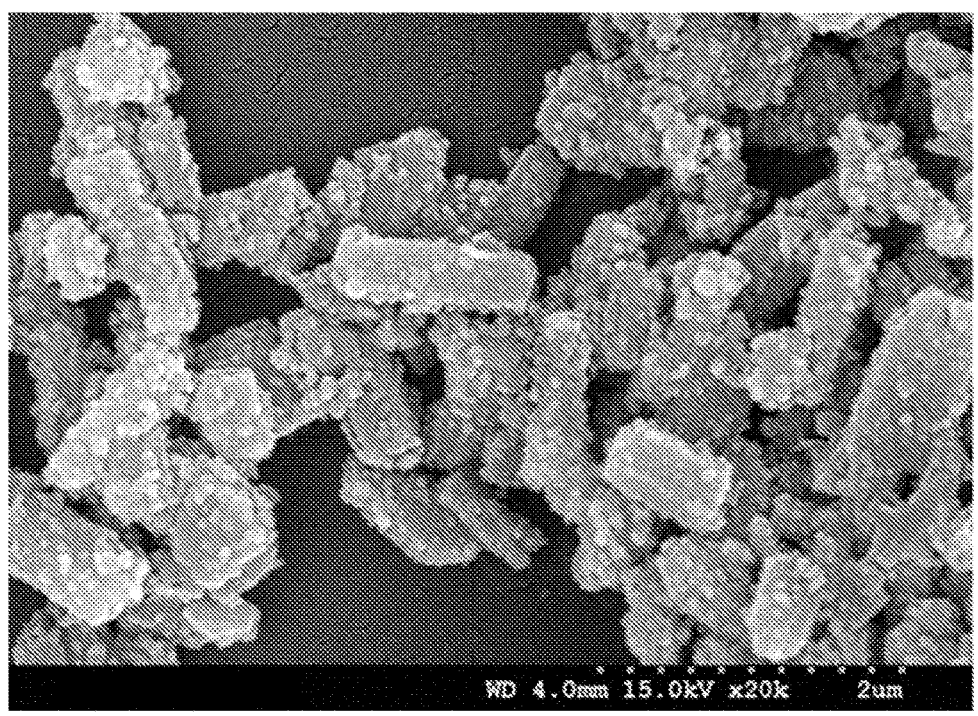
FIG. 6 shows a micrograph of zinc pyrithione particles encapsulated with a silicon-containing polymeric structure made in accordance with Example 3.

Example 3. Preparation of Silica-Coated/Encapsulated Zinc Pyrithione in Ethanol About 30 g of Zinc pyrithione particles and 400 mL of 2% PVP 360 in ethanol solution were placed in a 1 L round-bottom flask. The mixture was sonicated by probe sonicator for 1 min. Then 5 mL of ammonium hydroxide was added into the Zinc pyrithione dispersion. After that, 21 g of TEOS was added. The mixture was agitated by overhead mixer at 600 rpm for 16 h and said microcapsules were obtained with silica shell and a ZPT core. The capsules had a particle size distribution of d (90%): 2.56 μm; d (50%): 1.56 μm; d (10%): 0.95 μm. The capsules contained Zinc pyrithione=75%, silica=25%. An SEM of the coated/encapsulated zinc pyrithione is shown in FIG. 6.

Example 4. Preparation of Silica-Coated/Encapsulated Zinc Pyrithione

About 3.0 g of Zinc pyrithione particles and 40 mL of 2% PVP-40 (Polyvinylpyrrolidone; Mw: 40,000) in an aqueous solution were placed in a 125 mL round-bottom flask. The mixture was sonicated by probe sonicator for 1 min. Then the obtained dispersion was titrated to pH 4.53 with 10% acetic acid under magnetic stirring. After that, 4.0 g of TEOS was added. The mixture was agitated by overhead mixer at 600 rpm for 16 h and said microcapsules were obtained with silica shell and a ZPT core. The capsules had a particle size distribution of d (90%): 2.76 μm; d (50%): 1.52 μm; d (10%): 1.52 μm.

TABLE 1

| Sample | Reaction Temperature | Product % by weight | | | Particle Size Distribution (μm) | | | Degradation Temp (° C.) |
| --- | --- | --- | --- | --- | --- | --- | --- | --- |
| | | ZPT | Water | Silica | d10 | d50 | d90 | |
| A (comp) | RT | 99% | 1% | 0% | 0.7 | 1.2 | 1.9 | 265 |
| B | RT | 88.4% | 0.7% | 10.9% | 0.9 | 1.5 | 2.2 | 280 |
| C | RT | 89.5% | 0.5% | 10% | 0.9 | 1.2 | 2.1 | 279 |
| D | RT | 88.4% | 0.9% | 10.7% | 0.8 | 1.3 | 2.1 | 283 |
| E | RT | 89.7% | 1.0% | 9.3% | 1.0 | 1.6 | 2.5 | 280 |
| F | RT | 88 | 0 | 12 | — | 1.5 | — | 280 |
| G | RT | 80 | 0 | 20 | — | 1.7 | — | 296 |
| H | RT | 75 | 0 | 25 | — | 2.9 | — | 297 |
| I | 60 C. | 68 | 0 | 32 | — | 3.3 | — | 294 |
| J | 60 C. | 57 | 0 | 43 | — | 5.1 | — | 294 |

Example 5. Preparation of Silica-Coated/Encapsulated Zinc Pyrithione in the Basic Medium About 3.00 g of ZPT particles and 40 mL of 2% PVP-360 in an aqueous solution were placed in a 125 mL glass jar. The mixture was stirred by silverson for 5 min at 5000 rpm to obtain uniformed Zinc pyrithione dispersion. Then the dispersion was titrated to pH 10.5 with ammonium hydroxide under magnetic stirring. After that, 1.68 g of TEOS was added. The mixture was stirred on a stir plate at 800 rpm for 23 h to obtain particles with silica shell and a ZPT core.

Example 6. Preparation of Silica-Coated/Encapsulated Zinc Pyrithione in the Presence of (CTAB)

About 30 g of Zinc pyrithione particles and 400 mL of 0.125% CTAB (cetyltrimethylammonium bromide) aqueous solution were placed in a 1 L round-bottom flask. The mixture was sonicated by probe sonicator for 1 min. Then the obtained dispersion was titrated to pH 4.51 with 10% acetic acid under magnetic stirring. After that, 15 g of TEOS was added. The mixture was agitated by overhead mixer at 600 rpm for 16 h and said microcapsules were obtained with silica shell and a ZPT core.

Example 7: Preparation of Silica-Coating Zinc Pyrithione Using Two-Step Addition of TEOS About 30 g of Zinc pyrithione particles and 400 mL of 2% PVP-17 in an aqueous solution were placed in a 1 L round-bottom flask. The mixture was homogenized by probe sonication for 80 seconds and then was stirred for 4 h on stir plate. After that, the dispersion was titrated to pH 4.53 with 10% acetic acid. Then 15.8 g of TEOS was added. The mixture was agitated by overhead mixer at 600 rpm for 16 h and then 10.5 g more of TEOS was added. The dispersion was continued to stir for 24 h. The microcapsules with thick silica layer were obtained. The capsules had a particle size distribution of d (90%): 8.7 µm; d (50%): 5.7 µm; d (10%): 3.6 µm. The capsules contained Zinc pyrithione=67.9%, silica=32%.

Example 8: Preparation of Silica-Coated/Encapsulated Zinc Pyrithione Using Two-Step Addition of TEOS About 30 g of Zinc pyrithione particles and 400 mL of PVP aqueous solution containing 1.5% PVP-17 and 1% PVP-360 were placed in a 1 L round-bottom flask. The mixture was homogenized by probe sonication for 70 seconds and then was stirred for 4 h on stir plate. After that, the dispersion was titrated to pH 4.53 with 10% acetic acid. Then 15.4 g of TEOS was added. The mixture was agitated by overhead mixer at 600 rpm for 16 h and then 10.3 g more of TEOS was added. The dispersion was continued to stir for 24 h. The microcapsules with thick silica layer were obtained. The capsules had a particle size distribution of d (90%): 7.3 µm; d (50%): 3.2 µm; d (10%): 1.4 µm. The capsules contained Zinc pyrithione=67.2%, silica=31%.

Example 9: Preparation of Silica-Coated/Encapsulated Zinc Pyrithione

About 13 g of ZnPT particles and 200 mL of PVP aqueous solution containing 1.5% PVP-17 were placed in a 500 mL round-bottom Jacketed flask. The mixture was homogenized by Silverson at 5000 rpm for 10 min and then was stirred for 4 h on stir plate. After that, the dispersion was titrated to pH 4.5 with 10% acetic acid. Then 12 g of TEOS was added. The mixture was heated to 60° C. and agitated by overhead mixer at 600 rpm for 6 h. The microcapsules with thick silica layer were obtained. The capsules had a particle size distribution of d (90%): 7.0 µm; d (50%): 4.0 µm; d (10%): 1.5 µm. The capsules contained ZnPT=72.4%, silica=27.6%.

Example 10: Preparation of Silica-Coated/Encapsulated Tebutryn

About 12 g of Terbutryn particles and 240 mL of 0.032%, CTAB (cetyltrimethylammonium bromide) aqueous solution were placed in a 1 L round-bottom flask. The mixture was sonicated by probe sonicator for 1 min. Then another 240 mL of 1% PVP-17 aqueous solution was added. After that, the obtained dispersion was titrated to pH 4. with 10% acetic acid under magnetic stirring. Then, 6.09 g of TEOS was added. The 5 mixture was agitated by overhead mixer at 600 rpm for 16 h and another 6.00 g of TEOS was added. The mixture was continued to agitate for another 16 h. said microcapsules were obtained with silica shell and a Terbutryn core.

Example 11: Preparation of Silica-Coated/Encapsulated Diuron

About 12 g of Diuron particles and 240 mL of CTAB (cetyltrimethylammonium bromide) aqueous solution (0.032%, 0.1 mM NaCl) were placed in a 1 L round-bottom flask. The mixture was sonicated by probe sonicator for 1 min. Then another 240 mL of 1% PVP-17 aqueous solution was added. After that, the obtained dispersion was titrated to pH 4.4 with 10% acetic acid under magnetic stirring. Then, 6.00 g of TEOS was added. The mixture was agitated by overhead mixer at 600 rpm for 16 h. Said microcapsules were obtained with silica shell and a Diuron core.

Example 12: Polyurethane Foam Containing Zinc Pyrithione

A Polyurethane foam formulation was prepared by Zinc pyrithione powder and encapsulated zinc pyrithione as prepared in Example 2 above. This is a conventional light density slab stock polyether TDI-based flexible foam using Lonza Poly G 32-52 polyol using the composition as shown in Table 2.

TABLE 2

| Biocide type | Control | ZnPt powder | Encapsulated ZnPt |
|---|---|---|---|
| Biocide active level (ppm) | 0 | 2000 | 2000 |
| Polyol Poly G 32-35 (g) | 150 | 150 | 150 |
| Water (g) | 6.6 | 6.6 | 6.6 |
| Niax L-618 Silicone surfactant (g) | 1.5 | 1.5 | 1.5 |
| Niax A-33 Amine catalyst (g) | 0.27 | 0.27 | 0.27 |
| Dabco T-9 Tin Based Catalyst (g) | 0.25 | 0.25 | 0.25 |
| toluene diisocyanate (g) | 82 | 82 | 82 |

In addition, a fourth composition using the antifungal ingredient Alphasan AF was also prepared under the same conditions. This Example demonstrates a positive impact of the encapsulated zinc pyrithione on minimizing the catalytic effect typically seen with standard zinc pyrithione. This positive effect is seen primarily in the reactivity rate (Table 3) (~30% improvement), air flow (Table 4) (~4× improvement), and rebound resilience (25.7% improvement) over un-encapsulated zinc pyrithione (Table 5).

TABLE 3

Reactivity

| Treatment | Reactivity Time (secs) |
| --- | --- |
| Negative Control | 96 |
| Zinc Pyrithione-Std | 87 |
| Zinc Pyrithione-Example 2 | 80 |
| Alphasan AF | 83 |

TABLE 4

Air Flow

| Treatment | Air Flow (cfm) | % Reduction |
| --- | --- | --- |
| Negative Control | 3.5 | Baseline |
| Zinc pyrithione-Std | 0.25 | 92.8 |
| Zinc pyrithione-Enc. | 1 | 71.4 |
| Alphasan AF | 1.2 | 65.7 |

TABLE 5

Rebound Resilience

| Treatment | Rebound (%) | % Reduction |
| --- | --- | --- |
| Negative Control | 35 | Baseline |
| Zinc pyrithione-Std | 15 | 42.9 |
| Zinc pyrithione-Enc. | 24 | 68.6 |
| Alphasan AF | 26 | 74.3 |

Example 13—Encapsulated Zinc Pyrithione in Polyvinyl Chloride

Flexible PVC films were prepared by dispersing the zinc pyrithione as shown in TABLE 6 into 36% plasticizer (Soft'n'Safe) and blending with 64% PVC powder such that the amount of the zinc pyrithione in the final film were the amounts shown in Table 6. The encapsulated zinc pyrithione used in this example was prepared in accordance with Example 1 above. 15 grams of blend were then pressed between 6" by 6" plates in a Carver press at 160° C. and 3000 psi for <1 minute. The color was measured using a BYK Spectro-Gloss Meter over white leneta board to determine the CIE L*a*b* color of each sample, the gloss, the ΔYE with respect to white, and the opacity via color over black leneta board. The data is listed in Table 6 and demonstrate that encapsulated zinc pyrithione as prepared according to the present invention does not yellow PVC as compared to un-encapsulated zinc pyrithione.

TABLE 6

| Sample | L | a | b | G | Delta-YE |
| --- | --- | --- | --- | --- | --- |
| Negatice control | 87.02 | 1.89 | 6.52 | 23.9 | 15.64 |
| 2000 ppm ZnPt | 88.68 | 0.24 | 8.67 | 26.4 | 18.12 |
| 2000 ppm Encapsulated ZnPt | 89.03 | −0.18 | 6.73 | 19.9 | 14.08 |

While the invention has been described above with references to specific embodiments thereof, it is apparent that many changes, modifications and variations can be made without departing from the invention concept disclosed herein. Accordingly, it is intended to embrace all such changes, modifications, and variations that fall within the spirit and broad scope of the appended claims.

What is claimed is:

1. A silicon-containing polymeric structure coated/encapsulated active ingredient comprising:
   (i) a solid active ingredient having an outer surface, wherein the active ingredient comprises pyrithione compounds, basic copper carbonate, isothiazolinone compounds, substituted triazines, carbamates, triazoles and combinations thereof;
   (ii) a surfactant applied to the outer surface; and
   (iii) silicon-containing polymeric structure applied to the surfactant such that the silicon-containing polymeric structure at least partially surrounds the active ingredient and wherein the silicon-containing polymeric structure comprises pores therein.

2. The silicon-containing polymeric structure coated/encapsulated active ingredient according to claim 1, wherein the active ingredient comprises a metal pyrithione.

3. The silicon-containing polymeric structure coated/encapsulated pyrithione compound according to claim 2, wherein the metal is selected from the group consisting of zinc, copper and zirconium.

4. An antimicrobial polymer composition comprising a polymer matrix having a silicon-containing polymeric structure coated/encapsulated pyrithione compound according to claim 1 dispersed in the polymer matrix.

5. The antimicrobial polymer composition according to claim 4, wherein the polymer matrix comprises a chlorine containing polymer.

6. The antimicrobial polymer composition according to 5, wherein the polymer matrix comprises polyvinylchloride.

7. The antimicrobial polymer composition according to claim 4, wherein the polymer matrix comprises a polyurethane.

8. A molded article comprising the antimicrobial polymer composition according to claim 4.

9. The foam comprising the antimicrobial polymer composition according to claim 7.

10. A coating composition for coating a substrate, wherein the composition comprises the silicon-containing polymeric structure coated/encapsulated pyrithione according to claim 4.

11. A method of preparing a silicon-containing polymeric structure coated/encapsulated active ingredient, said method comprising:
   (i) providing a solid water-insoluble active ingredient, wherein the active ingredient comprises pyrithione compounds, basic copper carbonate, isothiazolinone compounds, substituted triazines, carbamates, triazoles and combinations thereof;
   (ii) dispersing the active ingredient in a liquid medium in which the active ingredient is insoluble to form a suspension of the active ingredient;
   (iii) adding a silicon-containing precursor for the polymeric structure to the suspension; and
   (iv) reacting the silicon-containing precursor to form the silicon-containing polymeric structure, wherein the silicon-containing polymeric structure is formed around the active ingredient, thereby forming a silicon-containing polymeric structure coated/encapsulated active ingredient and wherein the silicon-containing polymeric structure comprises pores therein.

12. The method according to claim 11, wherein said dispersing comprises mixing the active ingredient with a dispersant and water to form a mixture and mixing the mixture for a period of time to form a suspension the active ingredient in water.

13. The method according to claim 11, further comprising adjusting the pH of the suspension of the active ingredient to a pH within a range of about 3 to about 6 or from about 8 to about 12.

14. The method according to claim 11, wherein the active ingredient comprises a pyrithione compound.

15. The method according to claim 11, wherein the silicon-containing precursor comprises a silica precursor comprising silanes of the formula (I):

$$Si(Y)_m(X)_n \qquad (I)$$

wherein Y is a hydrolysable substituent and X is a substituent which is not reactive with the hydrolysable substituent during the polymerization reaction; m is an integer from 2-4; n is an integer of 0-2; wherein m+n=4; and wherein the average value of m is at least three.

16. The method according to claim 11, further comprising isolating the silicon-containing polymeric structure coated/encapsulated active ingredient compound from the water.

17. The method according to claim 16, wherein the silicon-containing polymeric structure coated/encapsulated active ingredient is in powder form.

18. The method according to claim 11, wherein the active ingredient comprises zinc pyrithione, said dispersing comprises mixing the zinc pyrithione with a dispersant and water to form a mixture and mixing the mixture for a period of time to form a suspension the pyrithione compound in water; said mixing comprises, low shear mixing, high shear mixing or sonication.

19. A silicon-containing polymeric structure coated/encapsulated active ingredient prepared by the process of claim 11.

* * * * *